United States Patent
Mitsuhashi (10) Patent No.: US 9,523,659 B2
(45) Date of Patent: Dec. 20, 2016

(54) INFORMATION PROCESSING APPARATUS, INFORMATION PROCESSING METHOD, AND INFORMATION PROCESSING PROGRAM

(75) Inventor: Kenji Mitsuhashi, Saint Louis, MO (US)

(73) Assignee: CANON KABUSHIKI KAISHA, Tokyo (JP)

( * ) Notice: Subject to any disclaimer, the term of this patent is extended or adjusted under 35 U.S.C. 154(b) by 380 days.

(21) Appl. No.: 14/238,765

(22) PCT Filed: Aug. 30, 2012

(86) PCT No.: PCT/JP2012/072665
§ 371 (c)(1),
(2), (4) Date: Feb. 13, 2014

(87) PCT Pub. No.: WO2013/032031
PCT Pub. Date: Mar. 7, 2013

(65) Prior Publication Data
US 2014/0192615 A1 Jul. 10, 2014

(30) Foreign Application Priority Data
Sep. 1, 2011 (JP) .................................. 2011-190502

(51) Int. Cl.
*G01N 29/00* (2006.01)
*G01N 29/24* (2006.01)
(Continued)

(52) U.S. Cl.
CPC ......... *G01N 29/2418* (2013.01); *A61B 5/0095* (2013.01); *A61B 5/7203* (2013.01); *G01N 21/1702* (2013.01); *G01N 2021/1706* (2013.01)

(58) Field of Classification Search
CPC ........................... G01S 15/8965; G01N 29/069
See application file for complete search history.

(56) References Cited

U.S. PATENT DOCUMENTS

| 4,941,101 A * | 7/1990 | Crilly .............................. 702/32 |
| 5,615,675 A | 4/1997 | O'Donnell et al. .......... 600/425 |

(Continued)

FOREIGN PATENT DOCUMENTS

| CN | 101006917 | 8/2007 |
| CN | 101612036 | 12/2009 |
| WO | WO 2012/090742 A1 | 7/2012 |

OTHER PUBLICATIONS

Crilly, IEEE Transaction on instrumentation and measurement, vol. 51, No. 6, Dec. 2002.*

(Continued)

*Primary Examiner* — Luke Ratcliffe
*Assistant Examiner* — Hovhannes Baghdasaryan
(74) *Attorney, Agent, or Firm* — Fitzpatrick, Cella, Harper & Scinto (57) ABSTRACT

An information processing apparatus is provided, which includes: a signal initialization unit that acquires an initial value of a pressure signal that is obtained after receive, by a receiving unit, of an elasticity wave from an object; an impulse response initialization unit that acquires an initial value of an impulse response of the receiving unit; and an output unit that outputs a modified pressure signal, wherein the output unit has: a signal modifying unit that modifies the pressure signal in use of the impulse response; a signal constraining unit that modifies the pressure signal based on a plurality of constraint conditions; an impulse response modifying unit that modifies the impulse response; and an impulse response constraining unit that modifies the impulse response based on constraint conditions which are time-bandwidth characteristics, and wherein the output unit generates the modified pressure signal by iteratively executing the processes.

21 Claims, 5 Drawing Sheets

(51) Int. Cl.
*A61B 5/00* (2006.01)
*G01N 21/17* (2006.01)

(56) References Cited

U.S. PATENT DOCUMENTS 6,216,025 B1   4/2001   Kruger .................... 600/407
2009/0222065 A1   9/2009   Dlugos, Jr. et al. ........... 607/60

OTHER PUBLICATIONS

Y. Wang et al., "Photoacoustic Imaging with Deconvolution Algorithm", *Phys. Med. Biol.*, vol. 49, pp. 3117-3124 (Jun. 28, 2004).
P. Stepanishen et al., "Experimental Verification of the Impulse Response Method to Evaluate Transient Acoustic Fields", *J. Acoust. Soc. Am.*, vol. 69, No. 6, pp. 1610-1617 (Jun. 1981).
T. Lu et al., "Deconvolution Algorithm with LTI Wiener Filter in Photoacoustic Tomography", *Photonics and Optoelectronics*, 2009 SOPO Conference, pp. 1-4, (Aug. 14, 2009).
J.J. Anaya et al., "A Method for Real-Time Deconvolution", *IEEE Transactions on Instrumentation and Measurement*, vol. 41, No. 3, pp. 413-419 (Jun. 1, 1992).
T. Yoshimura et al., "Characteristics of Iterative Deconvolution Algorithm with Fast Convergence Speed of the Iterations", *Optics Communications*, vol. 133, No. 1, pp. 434-442 (Jan. 1, 1997).

\* cited by examiner

INFORMATION PROCESSING APPARATUS, INFORMATION PROCESSING METHOD, AND INFORMATION PROCESSING PROGRAM

TECHNICAL FIELD

The present invention relates to an information processing apparatus, an information processing method, and an information processing program.

BACKGROUND ART

A photoacoustic imaging technology has been developed in recent years. This technology uses a probe or other receiving unit with a receiving element to receive an acoustic wave (photoacoustic wave) and obtains a pressure signal of the acoustic wave, the acoustic wave being generated by a photoacoustic effect when a measuring object is irradiated with light. This technology, therefore, can obtain a three-dimensional pressure distribution or optical characteristic value distribution of the inside of the measuring object. In other words, reconstruction can be realized. Therefore, when the measuring object is a living body, this technology can be applied to a medical field where the inside of the living body is imaged in order to observe a tumor.

A pressure signal measured in photoacoustic imaging deteriorates due to the influence of an impulse response of a receiving unit. This consequently reduces the resolution and contrast of a three-dimensional pressure distribution image obtained as a result of reconstruction. The influence of the impulse response of the receiving unit needs to be eliminated in order to improve the resolution and contrast. The operation for removing the influence is mathematically equivalent to convolution inverse operation, which is called "deconvolution" operation.

Non Patent Literature 1 discloses an example of a deconvolution method used in photoacoustic imaging. Non Patent Literature 1 discloses a method for actually measuring an impulse response of a receiving unit to perform deconvolution on a pressure signal. More specifically, this method concentrates excitation light into a fine region and uses a pressure signal, which is generated from the region, as an approximate value of the impulse response.

CITATION LIST

Non Patent Literature

NPL 1: Wang et al., "Photoacoustic imaging with deconvolution algorithm," Phys. Med. Biol. 49 (2004) 3117-24

SUMMARY OF INVENTION

Technical Problem

The method disclosed in Non Patent Literature 1 needs to actually measure an impulse response. In order to accurately measure an impulse response of a receiving unit, generally, a known input signal including sufficient high-frequency components needs to be generated to accurately measure a response of the receiving unit. However, it is difficult to measure the response under the presence of noise.

Moreover, in actual application, the impulse response changes due to changes in the measurement environment or changes in the measuring equipment over time. Because the abovementioned method needs to measure an impulse response every time when there is a change, actual operation of the method is difficult.

The present invention was contrived in view of the problems described above, and an object thereof is to provide a technology for favorably carrying out deconvolution for removing the influence of an impulse response in photoacoustic imaging.

Solution to Problem

The present invention provides an information processing apparatus, comprising:
a signal initialization unit configured to acquire an initial value of a pressure signal that is obtained after receive, by a receiving unit, of an elasticity wave propagating from a measuring object and;
an impulse response initialization unit configured to acquire an initial value of an impulse response of the receiving unit; and
an output unit configured to output a modified pressure signal based on the initial value of the pressure signal and the initial value of the impulse response, wherein
the output unit has:
a signal modifying unit configured to modify the pressure signal in use of the impulse response;
a signal constraining unit configured to modify the pressure signal based on constraint conditions, which are high contrast properties, positivity, and frequency band characteristics;
an impulse response modifying unit configured to modify the impulse response in use of the pressure signal; and
an impulse response constraining unit configured to modify the impulse response based on constraint conditions which are time-bandwidth characteristics of the impulse response, and wherein
the output unit is configured to generate the modified pressure signal by iteratively executing processes of the signal modifying unit, the signal constraining unit, the impulse response modifying unit, and the impulse response constraining unit in accordance with a predetermined condition.

The present invention also provides an information processing method, comprising:
a signal initialization step in which an information processing apparatus acquires an initial value of a pressure signal that is obtained after receive, by a receiving unit, of an elasticity wave propagating from a measuring object and;
an impulse response initialization step in which the information processing apparatus acquires an initial value of an impulse response of the receiving unit; and
an output step in which the information processing apparatus outputs a modified pressure signal based on the initial value of the pressure signal and the initial value of the impulse response, wherein
the output step generates the modified pressure signal by executing the following steps iteratively according to a predetermined condition:
a signal modifying step in which the information processing apparatus modifies the pressure signal in use of the impulse response;
a signal constraining step in which the information processing apparatus modifies the pressure signal based on constraint conditions which are high contrast properties, positivity, and frequency band characteristics;

an impulse response modifying step in which the information processing apparatus modifies the impulse response in use of the pressure signal; and an impulse response constraining step in which the information processing apparatus modifies the impulse response based on constraint conditions which are time-bandwidth characteristics of the impulse response.

The present invention also provides an information processing program for causing an information processing apparatus to execute an information processing method having:

a signal initialization step of acquiring an initial value of a pressure signal that is obtained after receive, by a receiving unit, of an elasticity wave propagating from a measuring object;

an impulse response initialization step of acquiring an initial value of an impulse response of the receiving unit; and an output step of outputting a modified pressure signal based on the initial value of the pressure signal and the initial value of the impulse response, wherein the output step generates the modified pressure signal by executing the following steps iteratively according to a predetermined condition:

a signal modifying step of modifying the pressure signal in use of the impulse response;

a signal constraining step of modifying the pressure signal based on constraint conditions which are high contrast properties, positivity, and frequency band characteristics;

an impulse response modifying step of modifying the impulse response in use of the pressure signal; and an impulse response constraining step of modifying the impulse response based on constraint conditions which are time-bandwidth characteristics of the impulse response.

Advantageous Effects of Invention

The present invention can provide a technology for favorably carrying out deconvolution for removing the influence of an impulse response in photoacoustic imaging.

Further features of the present invention will become apparent from the following description of exemplary embodiments with reference to the attached drawings.

DESCRIPTION OF EMBODIMENTS

An embodiment of the present invention is described hereinafter with reference to the drawings.

The technology according to the present invention is applied when formatting a pressure signal before obtaining (reconstructing) a three-dimensional pressure distribution or optical characteristic value distribution of the inside of a measuring object in photoacoustic imaging. The present invention, therefore, can be implemented, not only as a photoacoustic imaging device, but also as an image processing apparatus or information processing apparatus incorporated in or connected to the acoustic imaging device. The present invention can also be realized as an image processing program or information processing program for causing an image processing apparatus or an information processing apparatus, such as a computer, to execute a process of each step according to the present invention. The present invention can also be realized as an image processing method or an information processing method performed by the image processing apparatus or the information processing apparatus in accordance with the program.

The photoacoustic imaging device obtains a source distribution (three-dimensional pressure distribution) of a pressure signal of an elasticity wave generated as a result of light radiation or an optical characteristic value distribution such as an absorption coefficient distribution derived from the source distribution. Substance concentration distributions such as an oxygen saturation distribution and oxygenated/reduced hemoglobin concentration distribution are obtained from the optical characteristic value distribution. Based on these various value distributions, image data related to the inside of the measuring object to be displayed by a display unit can be created, and imaging (reconstruction) can be performed for, for example, medical diagnostic purposes.

<Configuration and Function of Photoacoustic Imaging Device>

Figure 1:
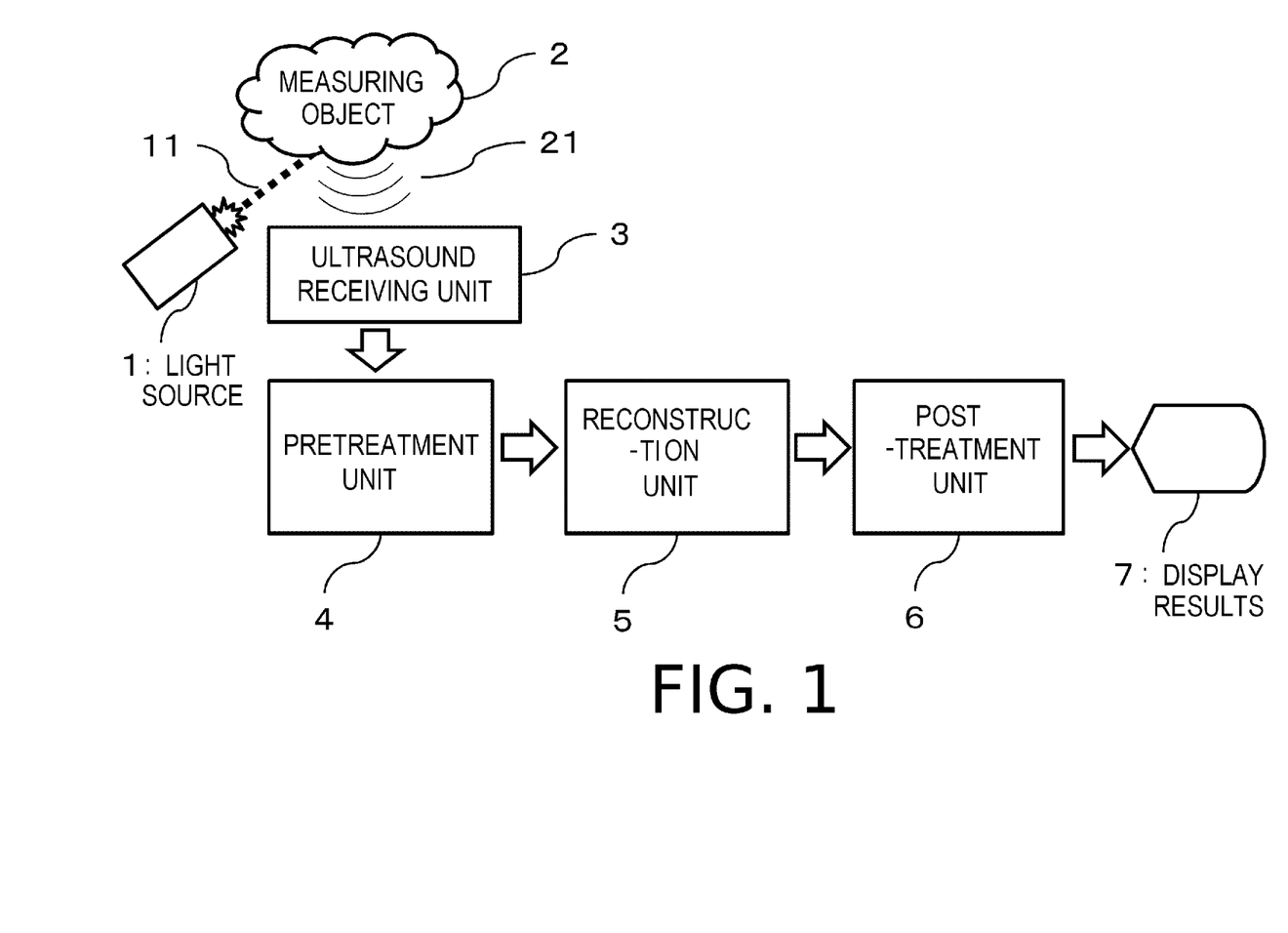
FIG. 1 is a schematic diagram of photoacoustic imaging device to which the present invention is applied.

FIG. 1 is a schematic diagram showing the entire photoacoustic imaging device that includes the embodiment of the present invention. Functions of the constituents of the photoacoustic imaging device are described hereinafter.

A light source 1 is a laser light source and lets a pulsed laser beam 11 come into a measuring object 2. When the measuring object is a living body, the light source radiates light of a wavelength that is absorbed by a specific component out of the components configuring the living body. The light source is preferably a pulsed light source that generates pulsed light in a several nanosecond to several hundred nanosecond order. Although it is preferred that the light source be a laser, a light-emitting diode and the like can be used in place of the laser. Various lasers such as a solid-state laser, gas laser, dye laser, semiconductor laser and the like can be used as the laser. It is preferred that the wavelength used by the light source be within a range of 700 nm to 1100 nm causing less light absorption in the living body. However, when obtaining the optical characteristic value distribution of a body tissue relatively close to a surface of the living body, the wavelength can be within a wider range of, for example, 400 nm to 1600 nm.

The measuring object 2 is an object that has an absorption coefficient distribution therein and absorbs the incoming light from the light source 1 in accordance with the absorption coefficient of each point inside the object. The energy of the absorbed light generates an elasticity wave in accordance with a Gruneisen coefficient of each point in the object, thereby generating a pressure distribution in the measuring object. This pressure distribution is called "three-dimensional pressure distribution" in the present description.

The three-dimensional pressure distribution generated in the measuring object 2 propagates in the form of an elasticity wave 21. The elasticity wave that reaches an ultrasound receiving unit 3 is measured and recorded as time-series pressure data. The pressure data is called "pressure signal" in the present description. The elasticity wave is also called "sound wave," "ultrasound wave," "acoustic wave," "photoacoustic wave," and "light induced ultrasound wave."

The ultrasound receiving unit is a detector for receiving the elasticity wave and converting it into an electric signal. The electric signal is subjected to AD conversion or amplification, if needed. A detector capable of receiving an elasticity wave of 100 KHz to 100 MHz, which is generated mainly from the measuring object, is preferably used as the ultrasound receiving unit. The ultrasound receiving unit may be a detector that uses a piezoelectric phenomenon, a detector that uses optical resonance, a detector that uses capacity changes, or any detector capable of receiving elasticity waves. Not only the time required for detection but also the influence of the vibration of the measuring object can be reduced by using the ultrasound receiving unit in which a plurality of receiving elements are arranged linearly or planarly. The ultrasound receiving unit corresponds to a receiving unit of the present invention.

A pretreatment unit 4 performs a pretreatment step, such as noise removal or deconvolution, on the pressure signal. The pretreatment unit is characterized by the present invention.

A reconstruction unit 5 performs a reconstruction step on the pretreated pressure signal. Reconstruction is a step of estimating a restoration of the three-dimensional pressure distribution from the pressure signal. The reconstruction unit corresponds to a constructing unit of the present invention.

A post-treatment unit 6 performs a post-treatment step, such as characteristics extraction and contrast adjustment on the reconstructed three-dimensional pressure distribution.

The pretreatment unit, the reconstruction unit, and the post-treatment unit can be realized as modules of programs executed by the information processing apparatus such as a computer. A dedicated circuit may be used as well.

The three-dimensional pressure distribution obtained as a result of the post-treatment is displayed by a display unit 7. As a result of these steps, information on the absorption coefficient distribution of the inside of the measuring object 2 can be made visible three-dimensionally.

The above has described a brief summary of the photoacoustic imaging device and its operations according to the embodiment of the present invention.

<Deconvolution Steps>

Figure 5:
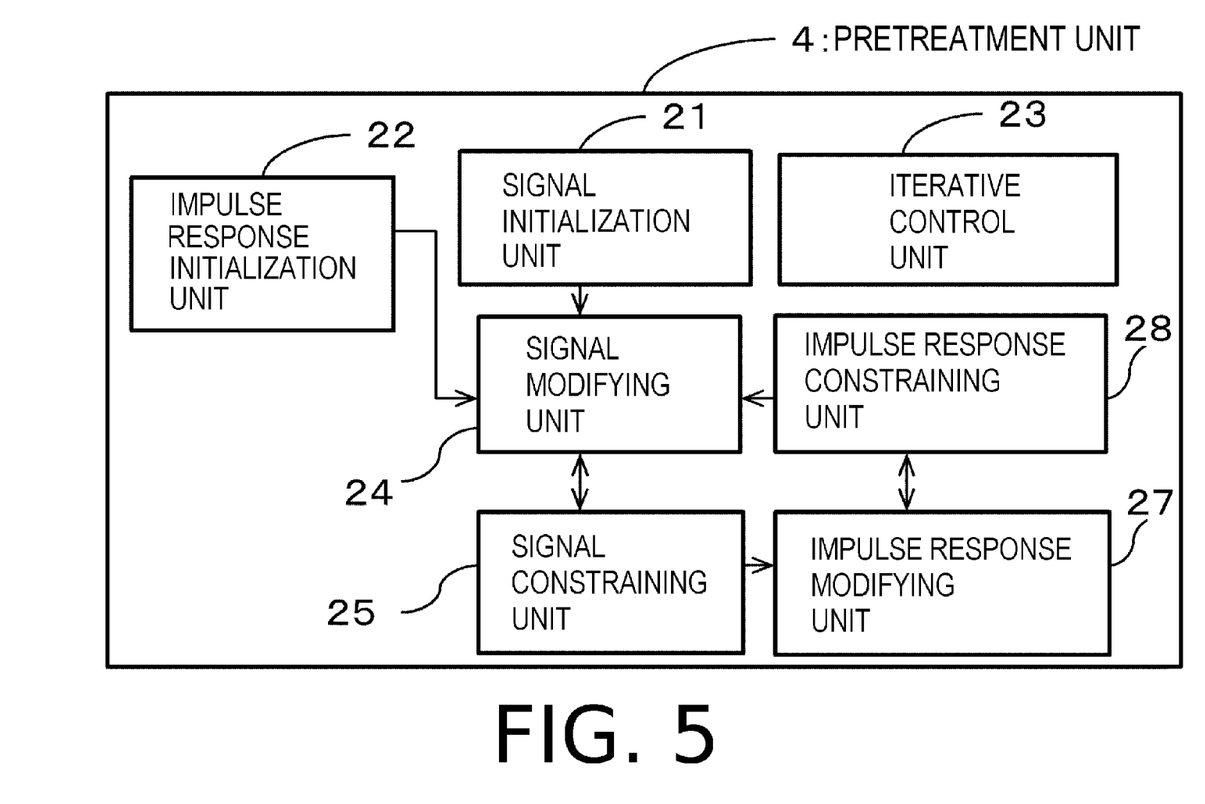
FIG. 5 is a schematic diagram showing a configuration of a pretreatment unit according to the present invention.

Each of steps carried out in the embodiment of the present invention are described hereinafter with reference to FIG. 2. In the following description, a pressure signal estimated value and impulse response estimated value are simply referred to as "signal" and "impulse response," respectively. The fact that the pressure signal and impulse response are estimated values is not explained unless otherwise specifically distinguished. The steps are carried out by the constituents of the pretreatment unit 4 as shown in FIG. 5.

First, in step S21, a signal initialization unit 21 acquires an actual measured value of the pressure signal from the receiving unit (y in the following equations (1) and (2)). An initial value of the signal ($x^0$ in Equation (1)) is set at 0.

Next, in step S22, an impulse response initialization unit 22 calculates or acquires an initial value of the impulse response ($h^0$ in Equation (2)). When calculating the initial value, for example, a damped oscillator model equivalent to the receiving unit in terms of frequency characteristics may be used to predict an approximate value of the impulse response. When acquiring the initial value, for example, an actual measured value of the impulse response including noise may be used as the approximate value. In other words, time-series data that qualitatively approximates the true impulse response may be used, and it is not necessary to change the initial value even when, for example, the impulse response slightly changes due to changes in the equipment over time.

In the next step S23, an iterative control unit 23 starts iterative calculation to deconvolute the signal. FIG. 2 shows a double loop of the iterative calculation. The double loop has, first, an internal loop (a first loop process) in which a process performed by a signal modifying unit and a process performed by a signal constraining unit are iterated, in this order, a predetermined number of times, the signal modifying unit and signal constraining unit being described hereinafter. The double loop also has another internal loop (a second loop process) in which a process performed by an impulse response modifying unit and a process performed by an impulse response constraining unit are iterated, in this order, a predetermined number of times. The double loop further has an external loop (a third loop process) in which these internal loops are carried out sequentially and iteratively. The processes performed by the double loop are described hereinafter.

However, this is merely an example of the embodiment, and the order and number of iterations can be changed appropriately, unless the essences of the processes performed by each modifying unit and each constraining unit are not undermined.

In the next step S24, the signal modifying unit 24 identifies the impulse response that is obtained at this moment, as a true value, and modifies the signal. The modification can be performed by means of, for example, Landweber iteration shown in Equation (1). Note that, in Equation (1), $x^k$ represents an estimated value of the signal obtained at the $k^{th}$ iteration, γ a relaxation coefficient, h the impulse response, y an actually measured pressure signal, * a complex conjugate, and a product symbol ($\otimes$) a convolution product.

[Math. 1]

$$x^{k+1} = x^k + \gamma h^* \otimes (y - h \otimes x^k) \quad (1)$$

The relaxation coefficient γ in Equation (1) is a coefficient for adjusting the speed of convergence of the iterations. A value obtained by dividing an actual value, larger than 0 and smaller than 2, by the maximum value of a power spectrum of the impulse response (the square of a Fourier transform absolute value), can be used as the relaxation coefficient. This value is defined by the fact that a spectral radius of an iterated map is smaller than 1 (convergence condition). Further, the larger the relaxation coefficient, the better, as long as the iterations can be performed stably.

In the next step S25, the signal constraining unit 25 re-modifies the signal based on constraint conditions such as the positivity, high contrast properties, and frequency band characteristics of the signal.

More specifically, the signal may be constrained by performing, for example, base line removal (corresponding to the high contrast properties), negative value removal (corresponding to the positivity), and high-frequency component removal (corresponding to the frequency band characteristics) in this order.

The base line removal may be performed by, for instance, multiplying the average value, median value, or low-frequency component of the signal by a predetermined coefficient and then subtracting the resultant value from the original signal. This process prevents the background of the signal from increasing during the iterative calculation and consequently guarantees the high contrast properties of the signal. Therefore, the predetermined coefficient may be an actual value of 0 or higher.

The negative value removal can be realized by simply substituting 0 for a negative part of the signal. This process is performed in order to guarantee a physical requirement in which a time integral (velocity potential) of the pressure signal needs to be positive value.

The high-frequency component removal may remove a high-frequency component of the signal by using, for example, a low pass filter characterized by an appropriate cutoff frequency. This process is performed in order to prevent high-frequency noise of the signal from increasing during the iterative calculation and defines an upper limit of the bandwidth of the modified signal. Therefore, it is preferred that the cutoff frequency be a value at least 1 time but no more than 10 times a frequency characterizing the center of the bandwidth of the receiving unit.

In the next step S26, the iterative control unit 23 performs iterative control described in step S23. When the condition for ending the pressure signal modification process is satisfied, the present flow is ended, and a reconstruction process is performed.

In the next step S27, an impulse response modifying unit 27 identifies the signal obtained at this moment, as a true value, and modifies the impulse response. The modification can be performed by means of, for example, Landweber iteration shown in Equation (2). Note that, in Equation (2), $h^k$ represents the impulse response obtained at the $k^{th}$ iteration, $\gamma$ a relaxation coefficient, x the signal, y an actually measured pressure signal, * a complex conjugate, and a product symbol ($\otimes$) a convolution product.

[Math. 2]

$$h^{k+1} = h^k + \gamma x^* \otimes (y - h^k \otimes x) \quad (2)$$

The condition for the relaxation coefficient in Equation (2) may be, as with the condition in step S24 described above, a coefficient for adjusting the speed of convergence of the iterations. A value obtained by dividing an actual value, larger than 0 and smaller than 2, by the maximum value of a power spectrum of the signal, can be used as the relaxation coefficient.

In the next step S28, an impulse response constraining unit 28 re-modifies the impulse response based on constraint conditions such as the time-bandwidth characteristics of the impulse response.

More specifically, the impulse response may be constrained by multiplying a damping function characterized by an appropriate cutoff time, by the impulse response. This process is performed in order to guarantee a physical requirement in which the impulse response attenuates within a finite period of time. Therefore, the cutoff time may be an indicator for a typical damping time of the impulse response. For example, the cutoff time may be calculated from the frequency characterizing the center of the bandwidth of the receiving unit and a Q value characterizing the bandwidth of the receiving unit.

Finally, returning to step S23, the iterative control unit 23 determines whether to end the iterative calculation or not. The iterative calculation may be ended once a predetermined number of iterations is accomplished or when the amount of modification obtained by the signal modifying unit or the impulse response modifying unit falls below a predetermined reference value. A combination of these conditions may be used. When the iterative calculation is not ended, the iterative calculation described above is continued.

The signal initialization unit 21, impulse response initialization unit 22, iterative control unit 23, signal modifying unit 24, signal constraining unit 25, impulse response modifying unit 27, impulse response constraining unit 28 in the present flow, configure part of the pretreatment unit 4. FIG. 5 shows this configuration. The iterative control unit 23 controls the other constituents by means of a control line, not shown. Each of the units can be configured as, for example, a part of the program realizing the pretreatment unit. Alternatively, a dedicated circuit may be used. In addition, the signal modifying unit, signal constraining unit, impulse response modifying unit, and impulse response constraining unit can be taken as an output unit for generating and outputting a modified pressure signal based on the initial value of the impulse response and the initial value of the pressure signal, the modified pressure signal being the pressure signal that is modified eventually.

As a result of these steps, the signal and the impulse response converge simultaneously into values that are the most possible under the constraint conditions. Note that the signal converges into the velocity potential of the pressure signal.

EXAMPLE

Next is described an example showing the deconvolution results calculated by the information processing apparatus according to the flow.

Measured data 1 was obtained as follows. A Ti:Sa laser (wavelength: 797 nm) was used as the light source. In order to obtain the measuring object, rubber wires having a 0.3-mm diameter were embedded at 5-mm intervals in an urethane gel block. A CMUT (Capacitive Micromachined Ultrasound Transducer) was used as the ultrasound receiving unit.

Measured data 2 was obtained as follows. A Ti:Sa laser (wavelength: 797 nm) was used as the light source. In order to obtain the measuring object, columnar optical absorbers (urethane gel applied with light absorbing ink) having a 2-mm diameter were embedded at 10-mm intervals in an urethane gel block. An ultrasound transducer using piezoelectric elements was used as the ultrasound receiving unit.

A known back projection method was used to perform reconstruction. Note that, because the present invention relates to formatting the pressure signal obtained prior to the reconstruction, the effects of the reconstruction can be exerted no matter what kind of reconstruction method is used. For instance, in place of the back projection method, a k-space method, a least-squares method, a constrained least-squares method, or a non-linear optimization method, may be used to perform the reconstruction.

Set values used are as follows. The initial value of the impulse response was calculated from the damped oscillator model. The relaxation coefficients $\gamma$ of the signal modifying unit and the impulse response modifying unit were obtained by dividing "1.9" by the maximum values of the power spectra of the impulse response and the signal. A method for multiplying the median value of the signal by 1 and then subtracting the resultant value from the original signal was adopted to perform the base line removal, which is performed by the signal constraining unit. The cutoff frequency used by the signal constraining unit was three times the central frequency of the bandwidth of the receiving unit. The cutoff time used in the impulse response constraining unit was 60 μs. Regarding the number of iterations, the signal modification and constraint loop were performed six times, and the impulse response modification and constraint loop were performed six times. A series of these processes were iterated sequentially 300 times.

Figure 2:
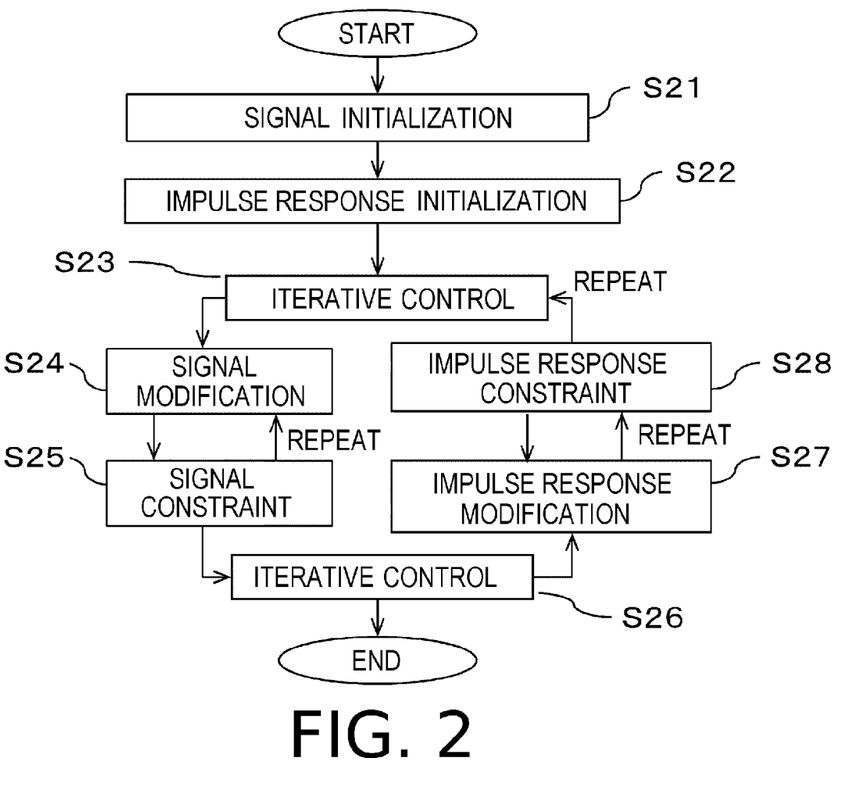
FIG. 2 is a flowchart showing steps of processes performed in an embodiment of the present invention.

Using these set values described above, the deconvolution was carried out according to the flowchart shown in FIG. 2.

Figure 3A:
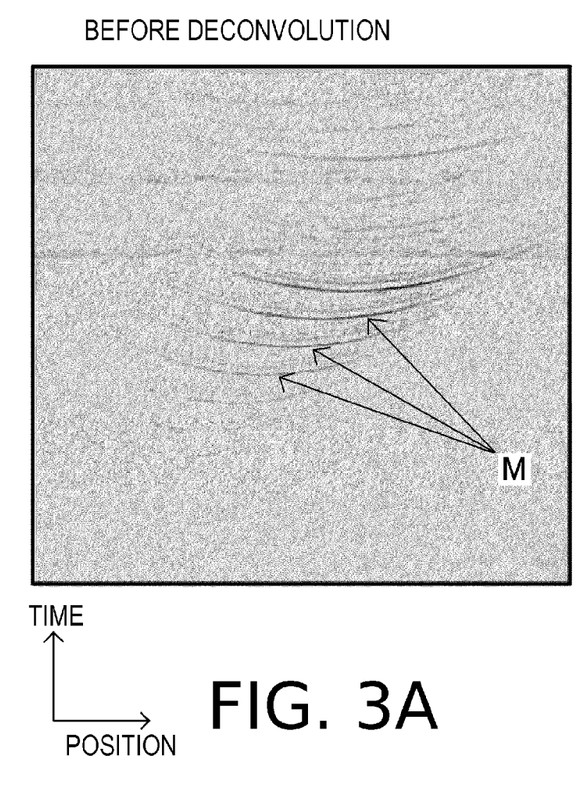
FIGS. 3A and 3B are diagrams comparing pressure signals obtained before and after the application of the present invention.
Figure 3B:
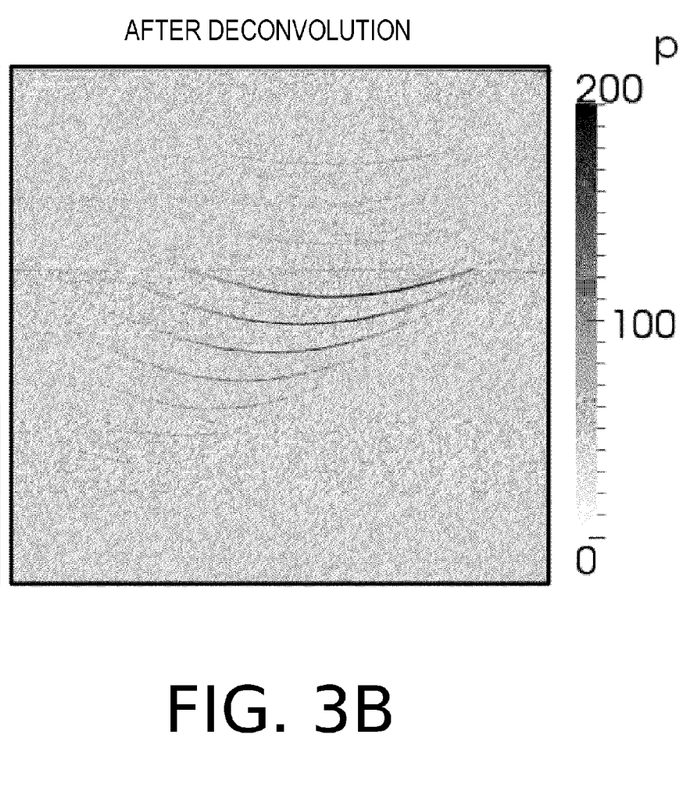

FIG. 3 shows the results of deconvolution performed on the measured data 1, the results being shown as pressure signals. In FIG. 3, each vertical axis represents time and each horizontal axis represents the positions of the receiving elements of the ultrasound receiving unit. The scale on the right-hand side illustrates the pressure (P) with respect to the color strength. As shown in FIG. 3(a), there are a plurality of peaks, which normally do not exist, prior to the deconvolution and at time after a main signal (shown by the arrows "M") is obtained. In FIG. 3(b), on the other hand, the peaks disappeared after the deconvolution was performed.

Figure 4A:
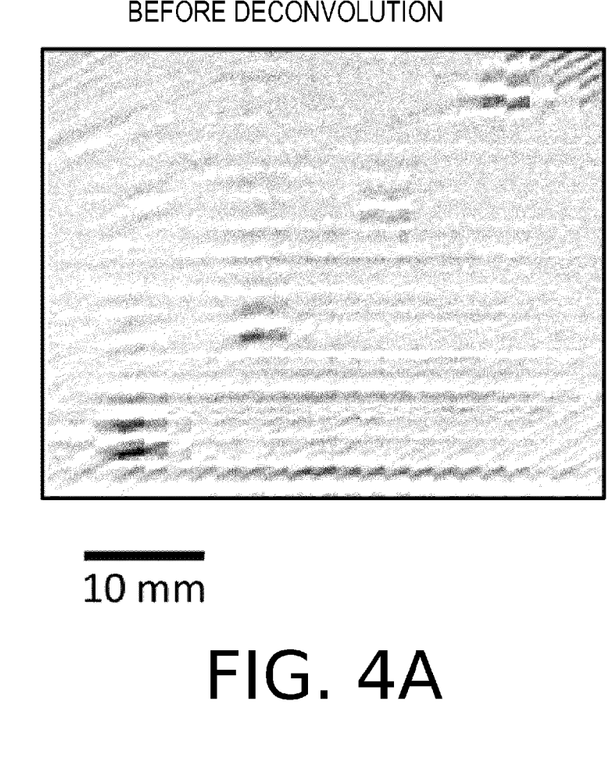
FIGS. 4A and 4B are diagrams comparing reconstruction results obtained before and after the application of the present invention.
Figure 4B:
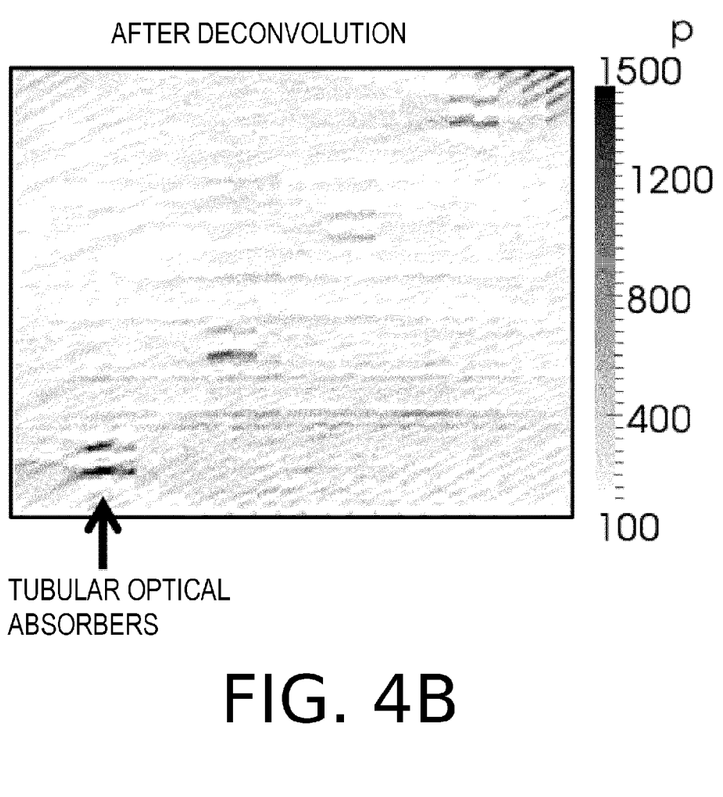

FIG. 4 shows the results of the deconvolution and reconstruction performed on the measured data 2. As shown in FIG. 4(a), the resolution and contrast are low prior to the deconvolution. In FIG. 4(b), on the other hand, the resolution and contrast improved after the deconvolution was performed.

The time required for the calculation was nine seconds in a 1.4 GFlops computing environment.

These results indicate that the deconvolution process according to the present invention can improve the resolution and contrast in photoacoustic imaging and achieve the object of the present invention.

The present invention was described above in detail with reference to the specific embodiment. However, the present invention is not limited to the specific embodiment, and the embodiment can be modified within the technical scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-190502, filed on Sep. 1, 2011, which is hereby incorporated by reference herein in its entirety.

The invention claimed is:

1. An information processing apparatus, comprising:
a signal initialization unit configured to acquire, as an initial value of a pressure signal, a pressure signal that is obtained by receiving, by a receiving unit, of an elasticity wave propagating from a measurement object;
an impulse response initialization unit configured to acquire an initial value of an impulse response of the receiving unit;
an output unit configured to output a modified pressure signal based on the initial value of the pressure signal and the initial value of the impulse response,
wherein said output unit further comprises:
a signal modifying unit configured to modify the pressure signal by using the impulse response;
a signal constraining unit configured to modify the pressure signal based on constraint conditions, wherein the constraint conditions include at least one of high contrast properties, positivity, and frequency band characteristics;
an impulse response modifying unit configured to modify the impulse response by using the pressure signal; and
an impulse response constraining unit configured to modify the impulse response based on constraint conditions which are time-bandwidth characteristics of the impulse response, and wherein said output unit is configured to generate the modified pressure signal by iteratively executing processes of the signal modifying unit, the signal constraining unit, the impulse response modifying unit, and the impulse response constraining unit in accordance with a predetermined condition.

2. The information processing apparatus according to claim 1, wherein said impulse response initialization unit is configured to acquire the initial value of the impulse response by actually measuring the impulse response of the receiving unit or predicting an approximate value of the impulse response.

3. The information processing apparatus according to claim 1, wherein said signal modifying unit is configured to modify the pressure signal according to Equation (1):

[Math. 1]

$$x^{k+1} = x^k + \gamma h^* \otimes (y - h \otimes x^k) \quad (1)$$

where $x^k$ represents an estimated value of the pressure signal obtained at a $k^{th}$ iteration, $\gamma$ represents a relaxation coefficient, h represents the impulse response, y represents the initial value of the pressure signal as an actually measured pressure signal, * represents a complex conjugate, and a product symbol represents a convolution product.

4. The information processing apparatus according to claim 3, wherein a value obtained by dividing an actual value, which is larger than 0 and smaller than 2, by a maximum value of a power spectrum of the impulse response, is used as the relaxation coefficient of Equation (1).

5. The information processing apparatus according to claim 1, wherein said impulse response modifying unit is configured to modify the impulse response according to Equation (2):

[Math. 2]

$$h^{k+1} = h^k + \gamma x^* \otimes (y - h^k \otimes x) \quad (2)$$

where $h^k$ represents the impulse response obtained at the $k^{th}$ iteration, $\gamma$ represents a relaxation coefficient, x represents the pressure signal, y represents the initial value of the pressure signal as an actually measured pressure signal, * represents a complex conjugate, and a product symbol represents a convolution product.

6. The information processing apparatus according to claim 5, wherein a value obtained by dividing an actual value, which is larger than 0 and smaller than 2, by a maximum value of a power spectrum of the pressure signal of Equation (2), is used as the relaxation coefficient of Equation (2).

7. The information processing apparatus according to claim 1, wherein said signal constraining unit is configured to modify the pressure signal by performing, sequentially, base line removal corresponding to the high contrast properties, negative value removal corresponding to the positivity, and high-frequency component removal corresponding to the frequency band characteristics.

8. The information processing apparatus according to claim 7, wherein said signal constraining unit is configured to perform the base line removal by multiplying an average value, a median value, or a low-frequency component of the pressure signal by a predetermined coefficient and then subtracting a resultant value from the pressure signal.

9. The information processing apparatus according to claim 8, wherein the predetermined coefficient used in the base line removal is an actual value of 0 or higher.

10. The information processing apparatus according to claim 7, wherein said signal constraining unit is configured to perform the high-frequency component removal using a low pass filter having a predetermined cutoff frequency.

11. The information processing apparatus according to claim 10, wherein the predetermined cutoff frequency used in the high-frequency component removal is a value greater than 1 time but no more than 10 times a frequency of a center of a bandwidth of the receiving unit.

12. The information processing apparatus according to claim 1, wherein said impulse response constraining unit is configured to modify the impulse response by multiplying a damping function having a predetermined cutoff time by the impulse response.

13. The information processing apparatus according to claim 12, wherein the predetermined cutoff time used by said impulse response constraining unit is calculated from a frequency of a center of the bandwidth of the receiving unit and a Q value expressing the bandwidth of the receiving unit.

14. The information processing apparatus according to any one of claim 1, wherein said output unit is configured to perform control of the number of implementation and implementation order of:
   a first loop process in which said signal modifying unit and said signal constraining unit sequentially and iteratively modify the pressure signal;
   a second loop process in which said impulse response modifying unit and said impulse response constraining unit sequentially and iteratively modifies the impulse response; and
   a third loop process in which the first loop process and the second loop process are iteratively performed.

15. The information processing apparatus according to claim 14, wherein said output unit is configured to execute a predetermined number of times the first loop process, the second loop process, and the third loop processes.

16. The information processing apparatus according to claim 14, wherein said output unit is configured to execute the first loop process until an amount of modification of the pressure signal in the first loop process falls below a predetermined reference value.

17. The information processing apparatus according to claim 14, wherein said output unit is configured to execute the second loop process until an amount of modification of the impulse response in the second loop process falls below a predetermined reference value.

18. The information processing apparatus according to claim 1, further comprising:
   a constructing unit configured to construct image data related to the inside of the measurement object by using the modified pressure signal outputted by said output unit.

19. An information processing method, comprising:
   a signal initialization step in which an information processing apparatus acquires, as an initial value of a pressure signal, a pressure signal that is obtained by receiving, by a receiving unit, an elasticity wave propagating from a measurement object;
   an impulse response initialization step in which the information processing apparatus acquires an initial value of an impulse response of the receiving unit; and
   an output step in which the information processing apparatus outputs a modified pressure signal based on the initial value of the pressure signal and the initial value of the impulse response,
   wherein said output step includes generating the modified pressure signal by executing the following steps iteratively according to a predetermined condition:
       a signal modifying step in which the information processing apparatus modifies the pressure signal by using the impulse response;
       a signal constraining step in which the information processing apparatus modifies the pressure signal based on constraint conditions, wherein the constraint conditions include at least one of high contrast properties, positivity, and frequency band characteristics;
       an impulse response modifying step in which the information processing apparatus modifies the impulse response, by using the pressure signal; and
       an impulse response constraining step in which the information processing apparatus modifies the impulse response based on constraint conditions which are time-bandwidth characteristics of the impulse response.

20. A non-transitory computer-readable storage medium storing, in executable form, an information processing program for causing an information processing apparatus to execute an information processing method having:
   a signal initialization step of acquiring, as an initial value of a pressure signal, a pressure signal that is obtained by receiving, by a receiving unit, of an elasticity wave propagating from a measurement object;
   an impulse response initialization step of acquiring an initial value of an impulse response of the receiving unit; and
   an output step of outputting a modified pressure signal based on the initial value of the pressure signal and the initial value of the impulse response,
   wherein said output step includes generating the modified pressure signal by executing the following steps iteratively according to a predetermined condition:
       a signal modifying step of modifying the pressure signal by using the impulse response;
       a signal constraining step of modifying the pressure signal based on constraint conditions, wherein the constraint conditions include at least one of high contrast properties, positivity, and frequency band characteristics;
       an impulse response modifying step of modifying the impulse response by using the pressure signal; and
       an impulse response constraining step of modifying the impulse response based on constraint conditions which are time-bandwidth characteristics of the impulse response.

21. The information processing apparatus according to claim 1, wherein
   the signal modifying unit is configured to modify the initial value of the pressure signal by using the initial value of the impulse response to acquire a first modified value of the pressure signal,
   the signal constraining unit is configured to modify the first modified value of the pressure signal based on the constraint conditions to acquire a second modified value of the pressure signal,
   the impulse response modifying unit is configured to modify the initial value of the impulse response by using the second modified value of the pressure signal to acquire a first modified value of the impulse response, and
   the impulse response constraining unit configured to modify the first modified value of the impulse response based on the constraint conditions to acquire a second modified value of the impulse response.

* * * * *